(12) United States Patent
Razavi

(10) Patent No.: US 10,888,143 B2
(45) Date of Patent: Jan. 12, 2021

(54) ERGONOMIC WRISTBAND FOR A WRIST WEARABLE DEVICE SUCH AS A SMARTWATCH

(71) Applicant: Seyed Masood Razavi, Burnaby (CA)

(72) Inventor: Seyed Masood Razavi, Burnaby (CA)

(73) Assignee: SMART INTERNATIONAL ENTERPRISES INC., Burnaby (CA)

( * ) Notice: Subject to any disclaimer, the term of this patent is extended or adjusted under 35 U.S.C. 154(b) by 0 days.

(21) Appl. No.: 16/788,328

(22) Filed: Feb. 12, 2020

(65) Prior Publication Data

US 2020/0178654 A1 Jun. 11, 2020

(51) Int. Cl.
| | | |
|---|---|---|
| *A41D 20/00* | (2006.01) | |
| *A45F 5/00* | (2006.01) | |
| *A44C 5/00* | (2006.01) | |
| *A61B 5/024* | (2006.01) | |
| *A61B 5/00* | (2006.01) | |

(52) U.S. Cl.
CPC ............ *A44C 5/0053* (2013.01); *A41D 20/00* (2013.01); *A61B 5/02438* (2013.01); *A61B 5/681* (2013.01); *A45F 2005/008* (2013.01)

(58) Field of Classification Search
CPC .......... A61F 5/00; A61F 5/0118; A61F 5/013; A61F 5/05866; A45F 2005/008; A41D 19/0037; A41D 13/088
See application file for complete search history.

(56) References Cited

U.S. PATENT DOCUMENTS

| | | | | |
|---|---|---|---|---|
| 4,761,835 A | * | 8/1988 | Chen ................. | A41D 19/0027 2/160 |
| 4,864,658 A | * | 9/1989 | Russell .............. | G04B 47/025 2/160 |
| 5,160,314 A | * | 11/1992 | Peters ................. | A61F 5/0118 602/21 |
| 5,267,943 A | * | 12/1993 | Dancyger ........... | A61F 5/0118 602/20 |
| 5,313,667 A | * | 5/1994 | Levine ............... | A41D 13/088 2/16 |
| 5,435,007 A | * | 7/1995 | Kalvestran ......... | A41D 13/088 2/16 |
| 5,538,501 A | * | 7/1996 | Caswell ............. | A61F 5/0118 128/878 |
| 5,600,849 A | * | 2/1997 | Hu ..................... | A41D 13/088 2/16 |
| 5,749,841 A | * | 5/1998 | Moore ................ | A41D 13/088 602/20 |
| 5,813,050 A | * | 9/1998 | Popowski ........... | A41D 13/088 2/16 |
| 5,819,313 A | * | 10/1998 | McCrane ............ | A41D 13/088 2/16 |
| 5,873,130 A | * | 2/1999 | Lafferty ............. | A41D 13/088 2/159 |

(Continued)

*Primary Examiner* — Brian D Nash

(57) ABSTRACT

Presented is an ergonomic wristband or a watchband for a wrist wearable device such as a smartwatch. The proposed wristband is structurally designed in a way to position the face of the wrist wearable device in a natural line of sight or convenient line of sight for a wearer. The proposed wristband when worn by the wearer would require no rotation or least rotation of the wearer's hand while viewing the face/display portion of the wrist wearable device mounted over the wristband.

17 Claims, 11 Drawing Sheets

(56) References Cited

U.S. PATENT DOCUMENTS

| | | | | |
|---|---|---|---|---|
| 5,928,172 | A * | 7/1999 | Gaylord | A61F 5/0118 602/21 |
| 6,168,556 | B1 * | 1/2001 | Saavedra | A63B 21/4019 224/220 |
| 6,184,804 | B1 * | 2/2001 | Harrison | G06F 1/163 341/20 |
| 6,219,843 | B1 * | 4/2001 | Passi | A41D 13/065 128/879 |
| D604,778 | S * | 11/2009 | Chan | D2/614 |
| 8,191,210 | B2 * | 6/2012 | Devers | A44C 5/0053 24/265 WS |
| 9,144,168 | B2 * | 9/2015 | Sedillo | A45F 5/00 |
| 2004/0039315 | A1 * | 2/2004 | Goumas | A61F 5/0118 602/5 |
| 2004/0049141 | A1 * | 3/2004 | Slautterback | A61F 5/0118 602/21 |
| 2004/0262342 | A1 * | 12/2004 | Pringle | A45F 5/00 224/221 |
| 2011/0283432 | A1 * | 11/2011 | Best | A41D 13/088 2/16 |
| 2012/0317696 | A1 * | 12/2012 | Chapuis | A41D 19/0024 2/160 |
| 2013/0026248 | A1 * | 1/2013 | Paulsen | A45F 3/16 239/1 |
| 2017/0135840 | A1 * | 5/2017 | Williams | A61F 5/05866 |
| 2017/0258624 | A1 * | 9/2017 | Butler | A41D 13/015 |
| 2017/0333242 | A1 * | 11/2017 | Hoffman | A61F 5/0113 |
| 2017/0354528 | A1 * | 12/2017 | Lane | A61F 5/0118 |
| 2018/0110643 | A1 * | 4/2018 | Carlson | A61F 5/05866 |
| 2018/0168844 | A1 * | 6/2018 | Garcia | A61F 5/0118 |
| 2018/0289522 | A1 * | 10/2018 | Zhu | A61F 5/012 |
| 2018/0361219 | A1 * | 12/2018 | Korte | A63B 69/0046 |
| 2019/0037938 | A1 * | 2/2019 | Hong | A41D 13/081 |
| 2020/0078203 | A1 * | 3/2020 | Engelshoven | A61F 5/24 |
| 2020/0246656 | A1 * | 8/2020 | Parent, Jr. | A63B 21/4021 |

* cited by examiner

ERGONOMIC WRISTBAND FOR A WRIST WEARABLE DEVICE SUCH AS A SMARTWATCH

FIELD OF THE INVENTION

The present disclosure relates to wristbands, or watchbands in general, and particularly to an ergonomically designed wristband configured in a way to position the face of a wrist wearable device (such as a wristwatch, a smartwatch or other like wearable electronic devices) in a natural line of sight or convenient line of sight for a wearer during activities such as writing, holding a steering wheel of a vehicle, riding a bike, during running and so on.

BACKGROUND

Wristwatches or wristbands are known in the art and commonly includes a band that is known to be worn around a wearer's wrist. The common wristwatches or smartwatches, while generally considered as being convenient, has their own imperfections. For example, it is very common for the watchbands to allow the watch to rotate upon the wrist when being worn. As a result, when the wearer is required to see the time, it is required to return the face of the watch to the top of the wrist so that the face of the watch aligns in the natural line of sight. The rotation of the wrist to see the face of the watch can be frustrating and can be difficult as well, for example, when the wearer does not have a free hand available to adjust or rotate the wrist band (such as while riding a bike). Further, with such traditional watchbands, when the wearer is wearing gloves, or long sleeve shirts, the face of the watch is often concealed under the sleeve portion of the gloves or shirts.

Several efforts have been made in the past and proposals for different watchband structures are made for improvising viewing angle of the watch or to overcome above discussed problems. For example, U.S. Ser. No. 10/261,473 discloses a wristband adapted to position a watch face substantially over at least one of a lateral radial portion of a wrist of a user or an anatomical snuffbox of the user. U.S. Ser. No. 10/261,473 proposes the watchband that would enable placement of the watch face in a natural line of sight of the user.

U.S. Pat. No. 8,191,210 discloses a device holding structure that includes two bands being used in association with a watch. The two bands are of length such that when the watch is placed on the top or back of the wearer's hand, one of the bands passes between the wearer's thumb and index finger so that the clasp extends around the thumb and attaches to the element. Another band extends around the base of the thumb and attaches to the buckle of the second end at approximately the side of the hand below the individual's fifth or smallest finger. The plurality of aligned loop holes provide means for varying the length of the band in accordance with the circumference of the wearer's hand.

U.S. Pat. No. 7,959,351 discloses a hand worn watch apparatus provides a wrist band, an index band, and a thumb band for securing the pliable material to the delta area of a wearer's hand. With the proposed watch apparatus (one useful for people in sports as well as those driving a car), the wearer does not have to practice elbow abduction and forearm pronation to read the watch display.

US20170035190 discloses an on-hand attachment band that positions a computing device, smart watch, or conventional watch on a position in the hand to provide a preferable viewing angle. The on-hand attachment band positions a device on the top of the hand proximate the thumb.

Although, the aforementioned and many other watchband structures are proposed in the past, there still remains a need for an improved and ergonomical design for a wristband/watchband that can position the face of the wrist wearable device (such as a wristwatch, a smartwatch or other like electronic devices) in a natural or convenient line of sight for the wearer.

BRIEF SUMMARY

An object of this invention is to provide a wristband or a watchband configured to position a wrist wearable device (such as a wristwatch, a smartwatch or other like electronic devices) on a top portion of the wearer's hand near the thumb in a specific viewing angle so that the face of the watch or display of the watch is inlined to the natural line of sight of a wearer.

Another object of the present invention is to provide an ergonomically designed wristband made of durable and comfortable material. The proposed wristband or watchband is adapted for positioning the watch over the wrist such that it would require no rotation or least rotation of the wearer's hand while viewing the face/display portion of the wristwatch. Further, the positioning of the wristwatch and the face of the wristwatch is not obstructed by the sleeve portions of the gloves or shirts, when the gloves or long sleeve shirts are worn by the wearer.

Another objective of the present invention is to provide a watchband that's designed so that the watchband is visually aesthetically pleasing and at the same time is comfortable to the hands of the wearer.

Another objective of the present invention is to provide a watchband that places the face of the watch in a perfect viewing angle and is located over the radial artery present inside the wrist near the side of thumb. This placement of the watch (smartwatch in particular) over the radial artery enables one or more heart rate sensors of the watch to get activated in order to monitor pulse rate of the wearer to get a quick assessment of wearer's health.

Another objective of the present invention is to provide a watchband/wristband that's constructed in a way to facilitate the atmospheric air to flow in and moisture content nearby the surface area of the wrist (covered by the watchband) to flow out.

Embodiments of the present invention discloses an ergonomic wristband for a wrist wearable device. The wristband includes a main body comprising a top surface, a bottom surface, a first portion, a second portion, a third portion, a fourth portion, a fifth portion, and a sixth portion; a first band comprising a proximal end and a distal end, the first band is attached to the first portion of the main body at the proximal end, and includes a first set of loop holes extending between the proximal end and the distal end; and a second band comprising a near end and a far end, the second band is attached to the second portion of the main body and includes a second set of loop holes extending between the near end and the far end.

According to the embodiment, the wristband further includes at least one coupling used for releasably attaching the wrist wearable device in between the third portion and a point in proximity to the fifth portion of the main body such that a back portion of the wrist wearable device is laid over the sixth portion of the main body.

According to the embodiment, the fifth portion of the main body includes a first opening through which the distal end of the first band is inserted and looped around a wearer's wrist such that a first segment of the first band extends over a length of a second segment of the first band ensuring one of the loop holes from the first set of loop holes present in the first segment of the first band is received and retained by a first retainer member configured on one of the loop holes from the first set of loop holes present in the second segment of the first band.

According to the embodiment, the fourth portion of the main body comprising a second retainer member configured thereon, wherein the far end of the second band is looped around a wearer's thumb such that one of the loop holes from the second set of loop holes of the second band is received, and retained by the second retainer member. The wristband with the wrist wearable device, when worn by a wearer by looping and securing the first band around the wearer's wrist, and the second band around the wearer's thumb, the main body positions a face portion of the wrist wearable device in a natural line of sight or a very convenient line of sight for the wearer thereby preventing necessity of turning a wearer's arm to view the face portion of the wrist wearable device.

These and other features, advantages and objectives of the invention will become apparent from the detailed description below, in light of the accompanying drawings.

BRIEF DESCRIPTION OF THE ACCOMPANYING DRAWINGS

In the accompanying drawing.

Figure 13:
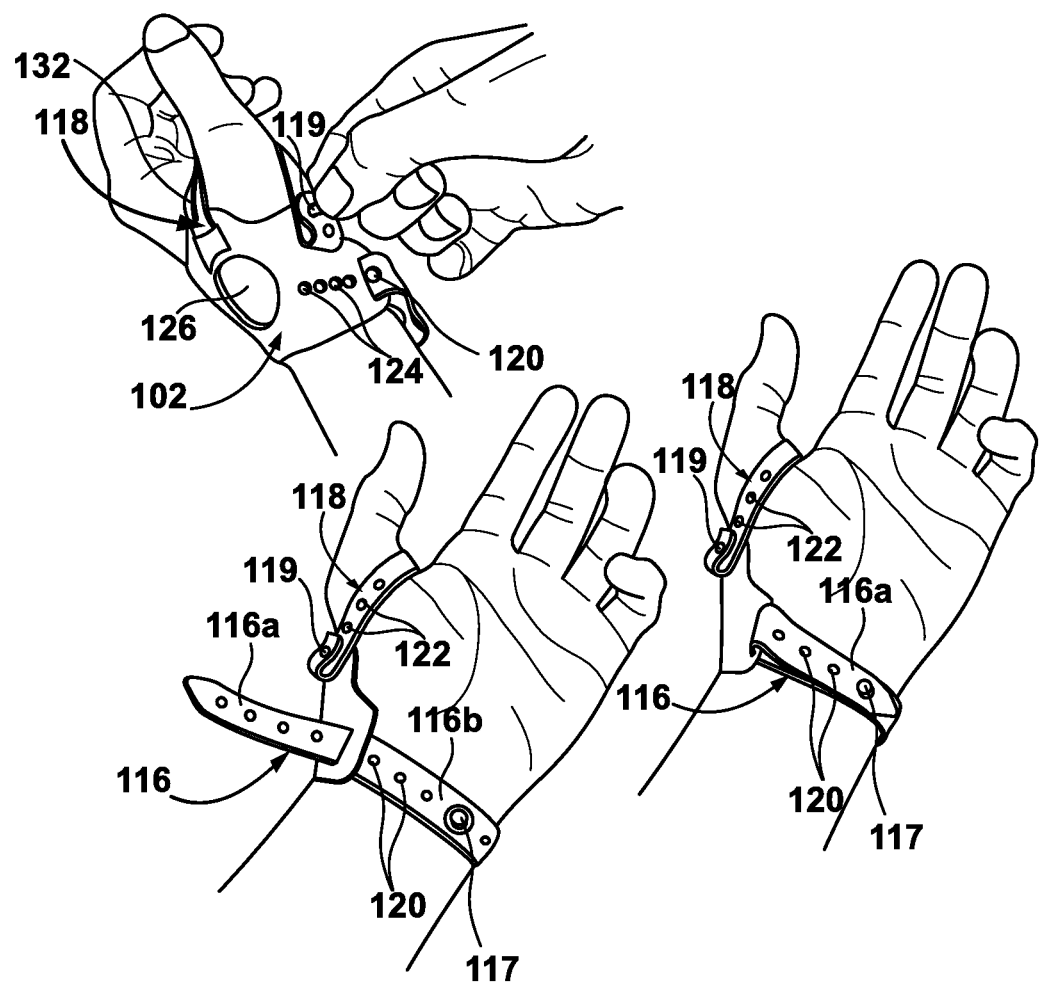
Figure 14:
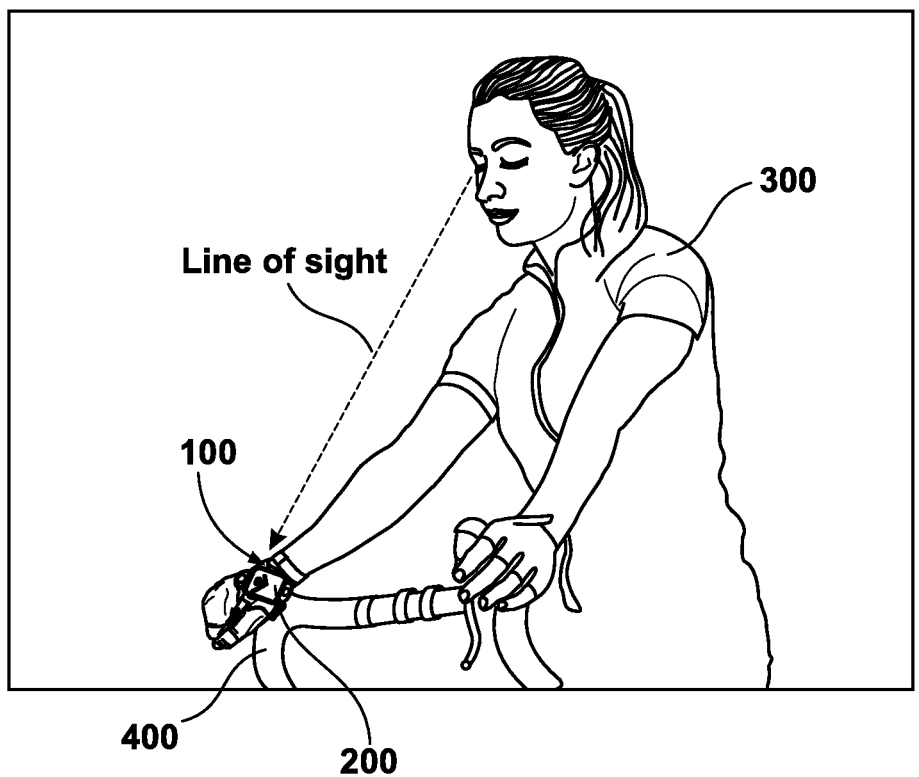

FIG. 13 illustrates a detailed visual representation of how the first and second band of the wristband are put around the wearer's wrist and thumb, when the wristband is worn by the wearer, according to an embodiment of the present invention; and FIG. 14 illustrates the wristband in use and the positioning of the face of the wrist wearable device (Eg. the smartwatch) in a natural line of sight or convenient line of sight for the wearer while riding a bike.

DETAILED DESCRIPTION

As used in the specification and claims, the singular forms "a", "an" and "the" include plural references unless the context clearly dictates otherwise. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. Those with ordinary skill in the art will appreciate that the elements in the figures are illustrated for simplicity and clarity and are not necessarily drawn to scale. For example, the dimensions of some of the elements in the figures may be exaggerated, relative to other elements, in order to improve the understanding of the present invention. References to "one embodiment", "an embodiment", "another embodiment", "an example", "another example", "some embodiment", and so on, indicate that the embodiment(s) or example(s) so described may include a particular feature, structure, characteristic, property, element, or limitation, but that not every embodiment or example necessarily includes that particular feature, structure, characteristic, property, element or limitation.

Before describing the present invention in detail, it should be observed that the present invention utilizes a combination of components which constitutes an ergonomically designed wristband configured in a way to position the face of a wrist wearable device (such as a wristwatch, a smartwatch or other like electronic devices) in a natural line of sight of a wearer/user. Accordingly, the components, their interconnectivity and operation have been represented, showing only specific details that are pertinent for an understanding of the present invention so as not to obscure the disclosure with details that will be readily apparent to those with ordinary skill in the art having the benefit of the description herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention. Further in the context of the present invention, the term "ergonomic curve" refers to the design of the main body of the wristband that conforms to the curve of the wearer's hand or a curve that makes wearer feel comfortable and pleasing to the wearer (or one that doesn't obstruct the wearer's hand movement), when the wristband is worn by the wearer. Further in the context of present invention, the terms "wristband,", and "watchband" are interchangeably used. Further, in the context of the present invention, the terms "watch,", "wristwatch,", "smartwatch,", "wrist wearable device," and "electronic device with display" and so on, are all interchangeably used.

The ergonomically designed wristband or wristwatch of the present invention, various embodiments associated therewith will now be discussed in detail with respect to the accompanying drawings FIGS. 1-14.

Figure 4:
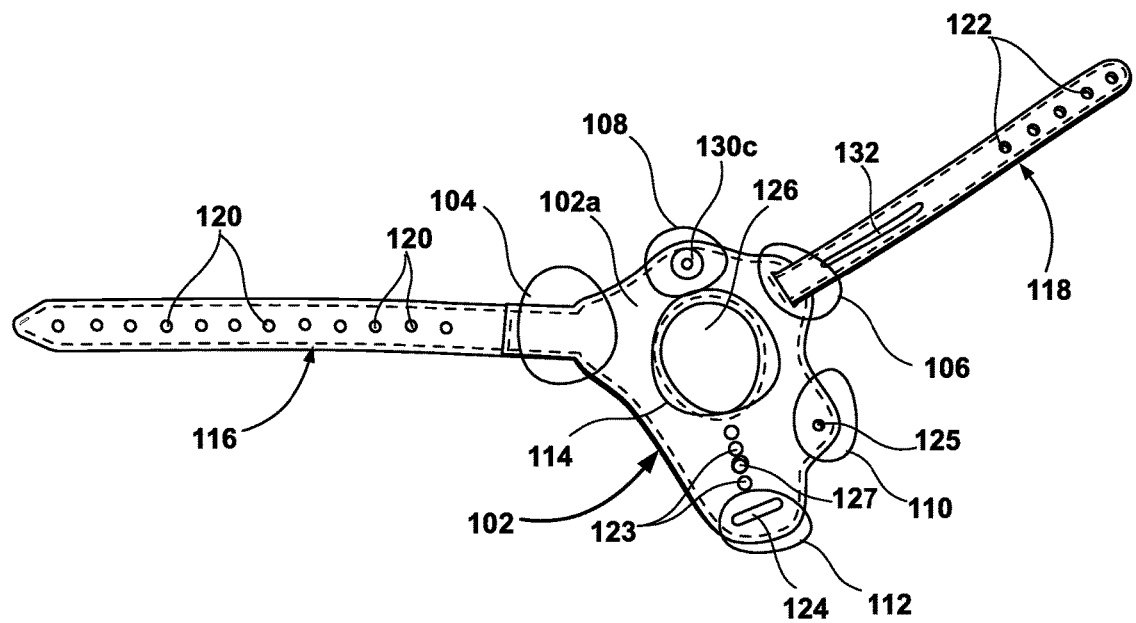
FIGS. 4-5 illustrates a top view and a bottom view of the wristband in a completely opened configuration with some of the components removed, according to an embodiment of the present invention.
Figure 5:
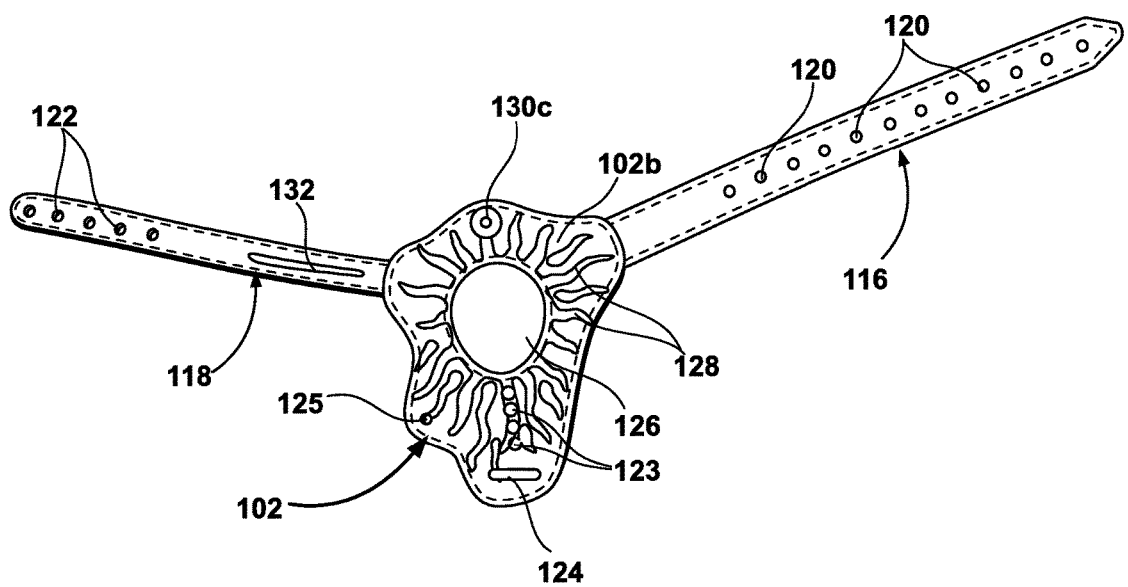
Figure 6:
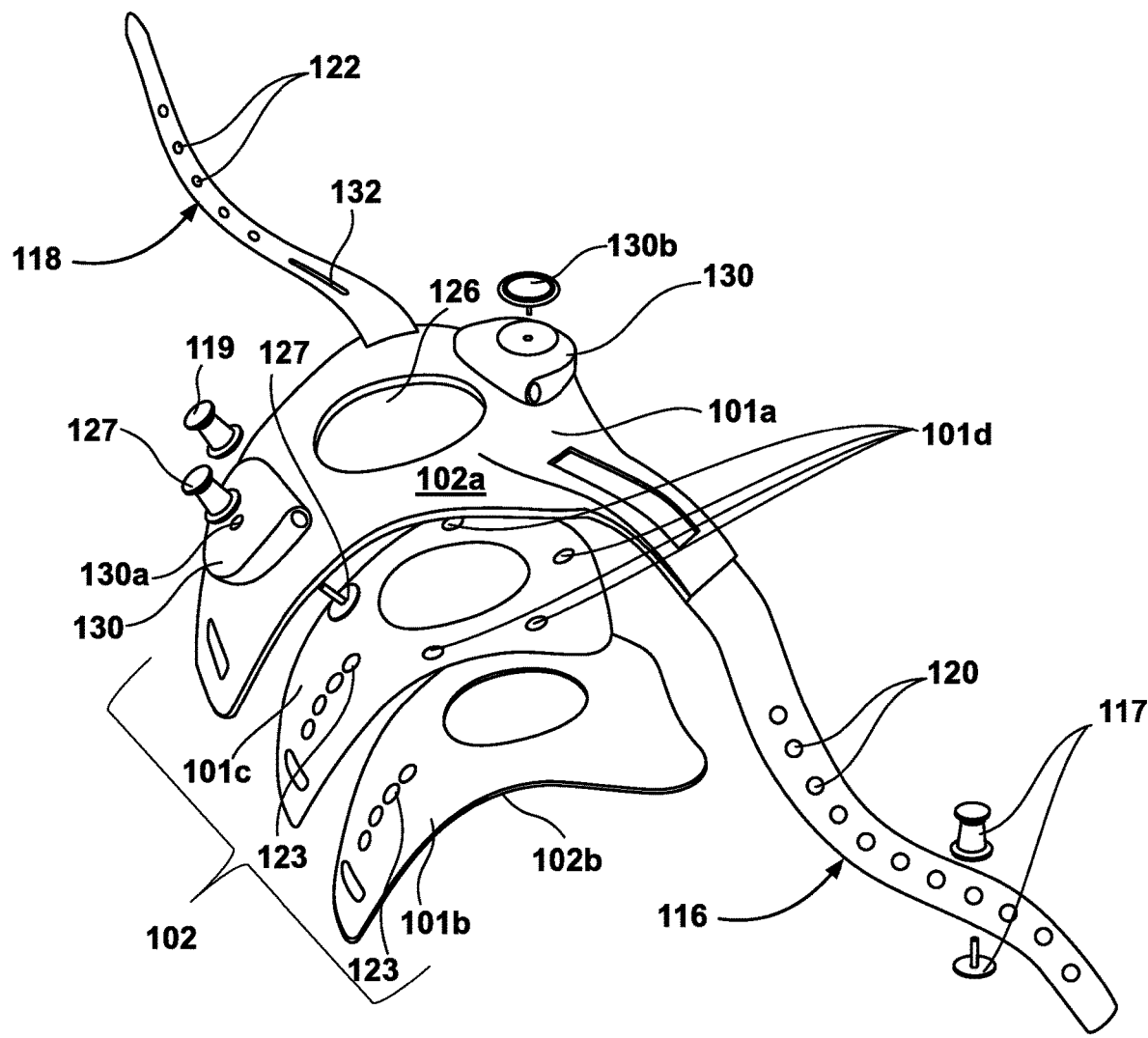
FIG. 6 illustrates an exploded view of the wristband of the present invention, according to an embodiment of the present invention.

Referring to accompanying figures, particularly FIGS. 1-5, the proposed wristband 100 includes a main body 102. The main body 102 includes a top surface 102a, a bottom surface 102b, a first portion 104, a second portion 106, a third portion 108, a fourth portion 110, a fifth portion 112, and a sixth portion 114. The main body 102 may be configured in variety of shapes, but according to the embodiment it is preferably shaped such that when the wristwatch 200 is laid completely over the main body 102, the wristwatch 200 do not extend beyond the surface area of the main body 102. According to an embodiment, the main body 102 of the wristband 100 is made of at least one layer. The main body 102 may be made of single layer, or multiple layers of suitable material may be attached to construct the main body 102. Particularly, as seen in FIG. 6, the main body 102 includes three layers, a first layer 101a, a second layer 101b, and a third layer 101c. These three layers 101a-101c constituting the main body 102 are substantially made similar in shape and size. In some embodiment, these layers might differ in shapes and sizes. In an embodiment, the first layer 101a and the second layer 101b are made identical in shape using same or different material. The material may include but not limited to natural leather, plastic, silicone, rubber, elastic polymer, or other suitable resilient material or any combinations thereof. The first layer 101a and second layer 101b are attached embodying the third layer 101c therebetween. The third layer 101c is made of preferably but not limited to a polycarbonate film and is laser cut to imitate the shape of the first and the second layers 101a and 101b. The layer 101c helps the wristband 100 in achieving an ergonomic curve (as seen indicated by double headed arrow in FIG. 11) over the wearer's wrist, when the wristband 100 is worn by the wearer 300. Further, the layer 101c assists the main body 102 of the wristband 100 to securely hold the wrist wearable device 200 in its position. In an embodiment, the layer 101c may be made in exact size/dimension as the layers 101a, and 101b. In some other embodiment, the layer 101c may be made in size/dimension slightly smaller compared to the layers 101a, and 101b. The layer 101c is preferably glued to attach to the layers 101a and 101b. The layer 101c may include a plurality of holes 101d to effectively pass the glue to undersides of the first layer 101a and the second layer 101b in order to facilitate effective attachment with the third layer 101c. According to the embodiment, the three layers 101a-101c are glued to attach together and the layers 101a and 101b are then sewn together at their boundary edges to further strengthen the attachment.

The wristband 100 further includes a first band 116 configured to loop around the wearer's wrist, when the wristband 100 is worn by the wearer as seen in FIG. 13. The band 116 includes a proximal end and a distal end. The band 116 is attached to the first portion 104 of the main body 102 at its proximal end. The proximal end of the band 116 may be either directly sewn at the first portion 104 of the main body 102 or may be first inserted inside the first layer 101a of the main body 102 and then sewn on the main body 102. Thus, it should be noted that there can be multiple ways to attach the proximal end of the band 116 to the first portion 104 of the main body 102. The band 116 includes a first set of loop holes 120 extending between its proximal end and the distal end. The band 116 further includes a first retainer member 117 (as seen in FIG. 3) that can be configured or releasably attached on a selected loop holes from the set of loop holes 120 of the first band 116.

Figure 1:
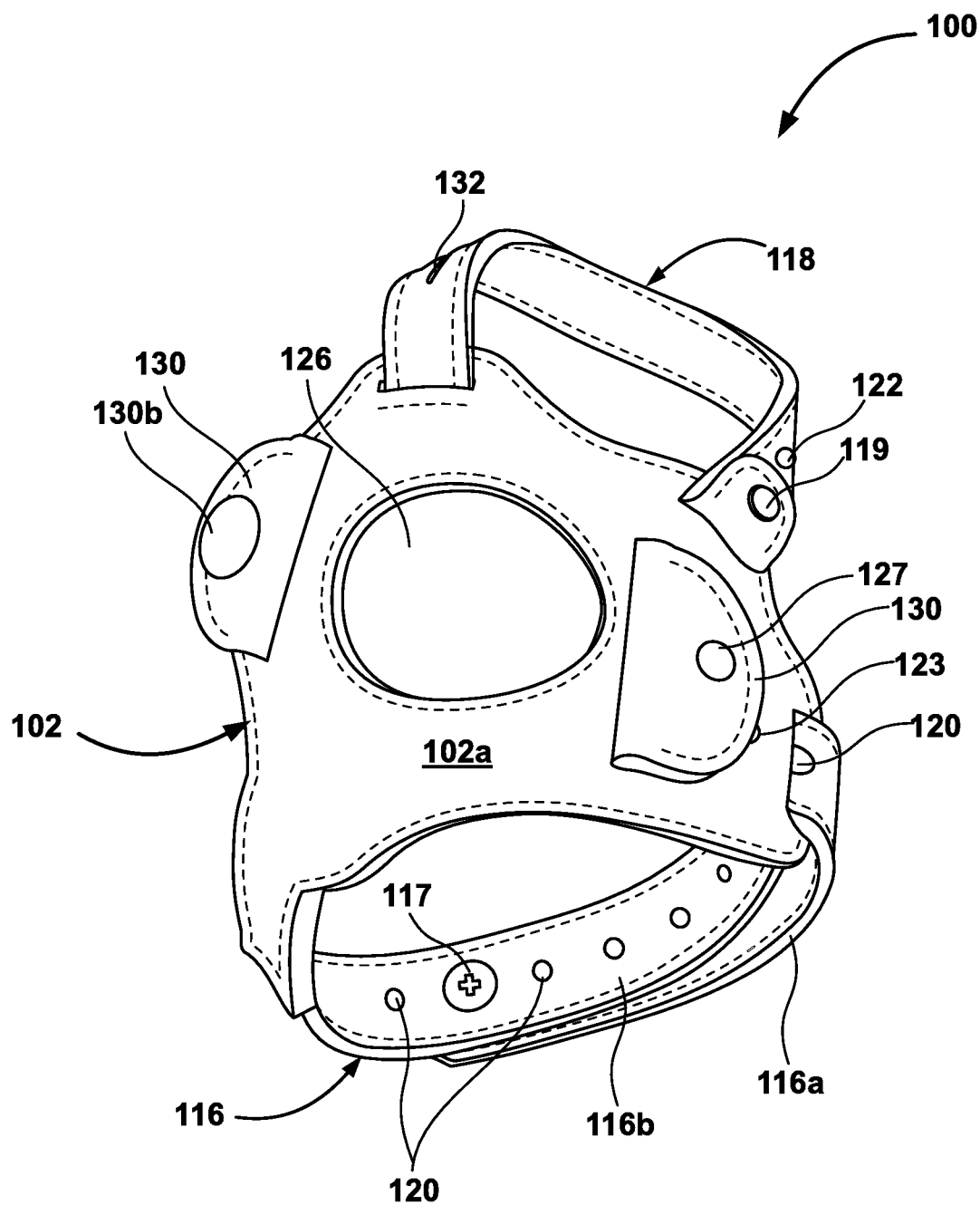
FIG. 1 illustrates a top perspective view of a wristband or watchband of the present invention without any wrist wearable device configured thereon, according to an embodiment of the present invention.
Figure 2:
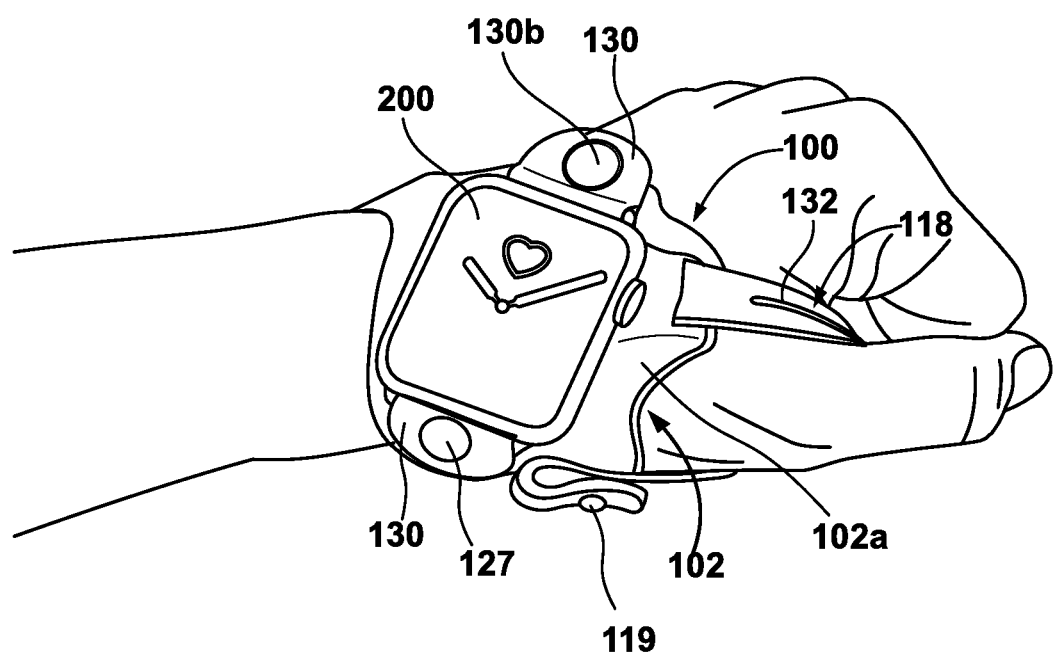
FIG. 2 illustrates the wristband of FIG. 1 with a smartwatch/wristwatch configured thereon and as seen worn by a wearer on his hand, according to an embodiment of the present invention.
Figure 12:
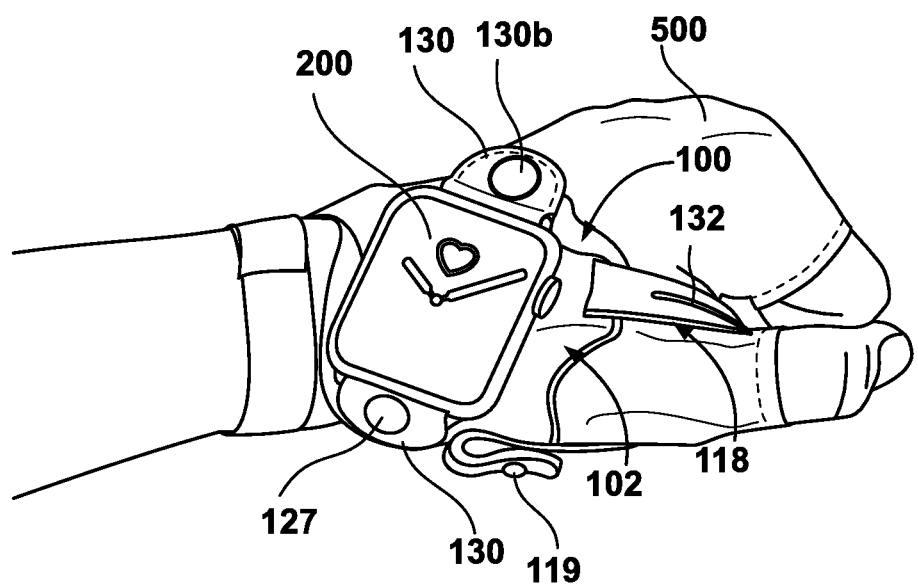
FIG. 12 illustrates the wristband of the present invention as seen being worn over a glove by the wearer, according to an embodiment of the present invention.

The wristband 100 further includes a second band 118 configured to loop around the wearer's thumb when the wristband 100 is worn by the wearer as seen in FIG. 13 and FIGS. 2 and 12. The band 118 includes a near end and a far end. The band 118 is attached to the second portion 106 of the main body 102. The near end of the band 118 may be either directly sewn at the second portion 106 of the main body 102 or may be first inserted inside the first layer 101a of the main body 102 and then sewn on the main body 102 (as seen in FIG. 4). Thus, it should be noted that there can be multiple ways to attach the near end of the band 118 to the portion 106 of the main body 102. The band 118 further includes a second set of loop holes 122 extending between its near end and the far end. The band 118 further includes an incision 132 of a predefined length made thereon in proximity to the second portion 106 of the main body 102 as seen in FIG. 4. The incision 132 present on the second band 118 helps the band 118 to retains flexibility and provide comfort to the wearer's thumb movement when the band 118 is looped and secured around the wearer's thumb.

Figure 3:
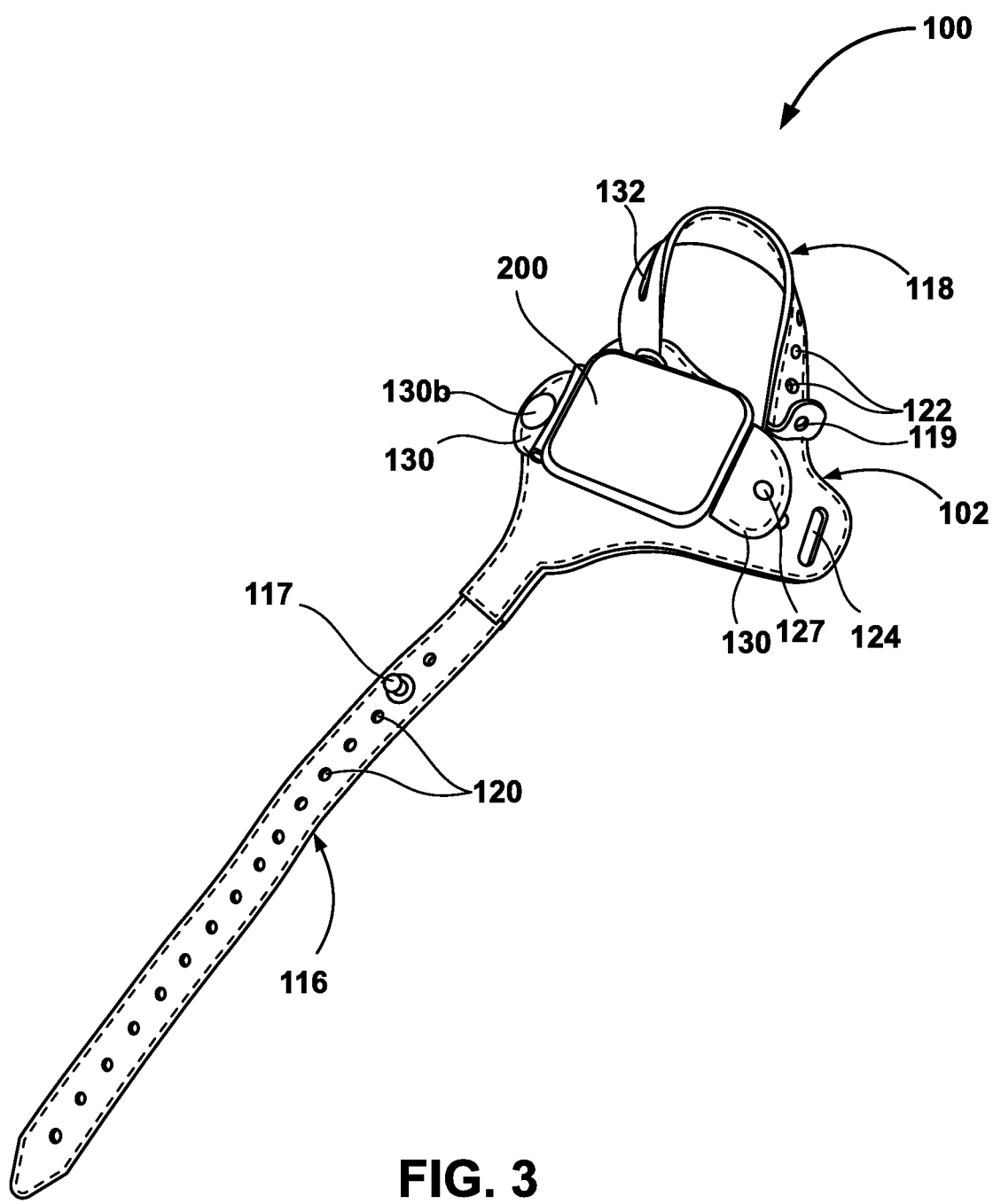
FIG. 3 illustrates a top view of the wristband of FIG. 1 with the smartwatch/wristwatch mounted thereon and a first band of the wristband in an opened configuration, according to an embodiment of the present invention.
Figure 9A:
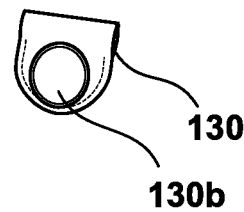
FIGS. 9A-9B illustrates a pair of couplings used for attaching the smartwatch/wristwatch over the main body of the wristband, according to an embodiment of the present invention.
Figure 9B:
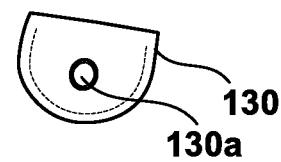
Figure 10:
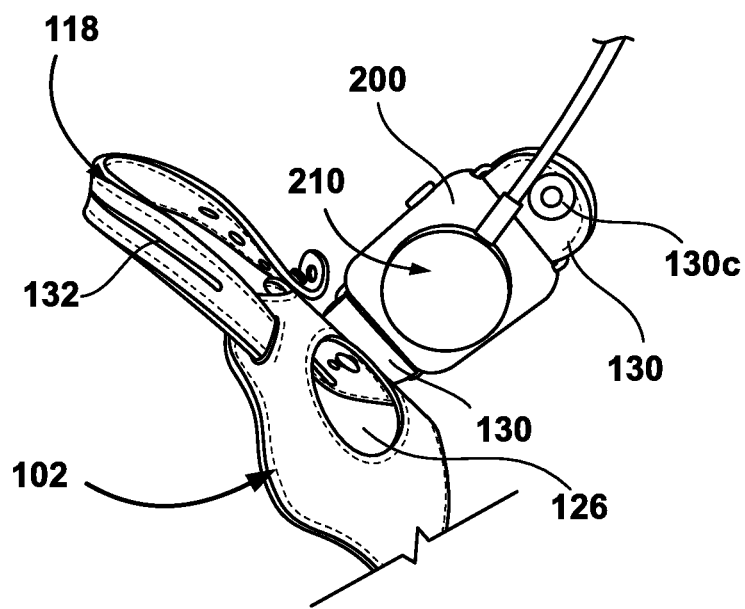
FIG. 10 illustrates partial detachment of the smartwatch from the main body of the wristband in order to facilitate charging of the smartwatch, according to an embodiment of the present invention.
Figure 11:
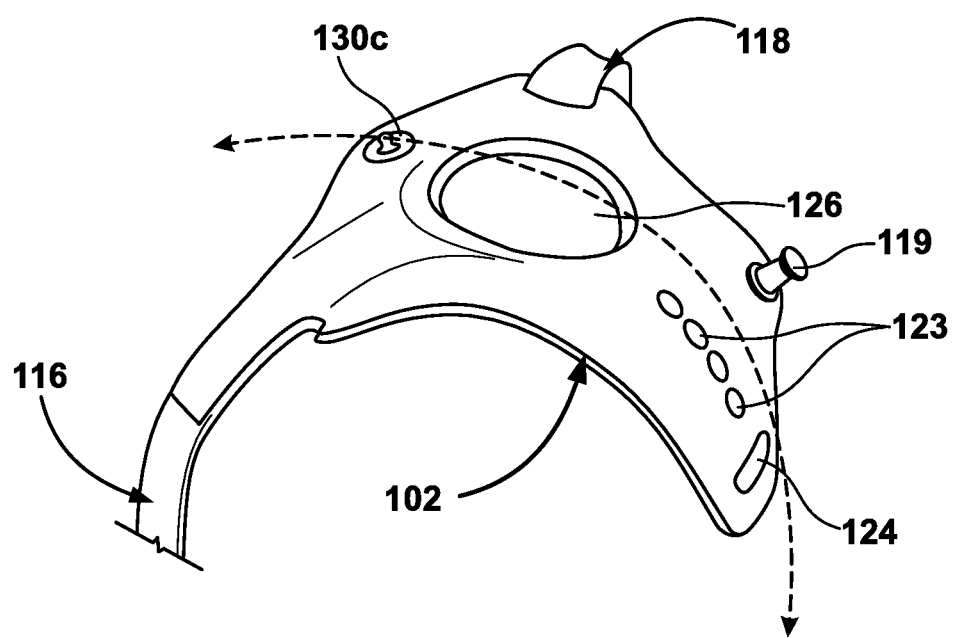
FIG. 11 illustrates an ergonomic curve of the main body portion of the wristband when worn by the wearer, according to an embodiment of the present invention.

According to the embodiments, the wristband 100 further includes at least one coupling 130 (as best seen in FIGS. 9A-9B) for releasably attaching the wrist wearable device 200 to the wristband 100 particularly in between the third portion 108 and a point in proximity to the fifth portion 112 of the main body 102 (as seen in FIGS. 2 and 3). The detachment of the wrist wearable device 200 from the wristband 100 may be required for various purposes, for example to replace an existing wrist wearable device 200 with a new one, for charging a smartwatch etc. FIG. 10 in particular shows partial detachment of the smartwatch 200 from the main body 102 so that an external charging cable or case 210 can be connected to the smartwatch 200. In the context of present invention, the wrist wearable device 200 may include but not limited to a wristwatch, a smartwatch, and any other like electronic device with a display. According to the embodiment, as shown in FIGS. 9A-9B, there may be two couplings 130 needed to connect the wrist wearable device 200 to the wristband 100. The coupling 130 may be configured in variety of shapes such as U shape, or some other shapes and made using same material as that of the wristband 100 or some other material such as plastic, or fabric. In the example shown, one of the coupling 130 (say a first coupling) may include a male portion 130b of a snap button that would connect to a female portion 130c of the snap button configured on the third portion 108 of the main body 102. This first coupling 130 snappingly attaches/connects one end of the wrist wearable device 200 to the third portion area 108 of the main body 102. According to the embodiment, another coupling 130 (say a second coupling of similar dimension or different dimension) may then be used to connect the other end of the wrist wearable device 200 to a point in proximity to the fifth portion 112. In the context of the present invention, the point in proximity to the fifth portion 112 herein refers to a hole selected from a set of holes 123 positioned in between the sixth portion 114 and the fifth portion 112 of the main body 102. Further according to the embodiment, a retainer member 127 may be selectively configured into one of the holes from the set of loop holes 123. According to the embodiment, the second coupling 130 may include a slot 130a that may be received and retained in place by the retainer member 127. Since multiple holes 123 are provided, these holes 123 helps in accommodating different sizes of the wrist wearable devices 200 in between the third portion 108 and the fifth portion 112 of the main body 102 (depending on which hole the wearer chooses to connect the retainer member 127).

In some other embodiment, both of these couplings 130 (the first and second coupling 130) connecting the watch 200 over the main body 102) may be made identical having snap buttons to fixedly attach a fixed size watch on the main body 102. In this scenario, the set of holes 123 may not be needed rather one can have a female portion of the snap button (similar to 130c) positioned to replace the holes 123 and the second coupling 130 will have a male portion of the snap button (just same as 130b) that would connect to the female portion 130c. In yet some other embodiment, both of these couplings 130 (the first and second coupling 130) connecting the watch 200 over the main body 102) may be made identical having a slot (similar to 130a) and be connected to the third portion 108 and the selected hole from the holes 123 using a retainer member (such as retainer member 127) that may be configured over the selected hole 123 and a hole (new hole) formed on the third portion 108. In this case, the female portion 130c of the snap button configured on the third portion 108 will be replaced by the new hole.

According to the embodiment, when the wrist wearable device 200 is attached over the wristband 100, the back portion of the wrist wearable device 200 is laid over the sixth portion 114 of the main body 102. In an embodiment, the main body 102 will embody an opening 126 configured on the sixth portion 114. The opening 126 configured on the sixth portion 114 of the main body 102 may be made substantially egg like in shaped or circular in shape or any other shapes. The opening 126 is preferably shaped such as to allow a portion of back of the smartwatch 200 to contact the wearer's skin or body positioned underside the smartwatch 200. In particular, when the wristband 100 is worn by the wearer with the smartwatch 200 positioned in a perfect viewing angle (or at line of sight of the wearer), then the opening 126 configured over the sixth portion 114 enables one or more heart rate sensors 202 (seen in FIG. 7) of the smartwatch 200 to contact the wearer's skin or radial artery to get activated to monitor pulse rate of the wearer to make a quick assessment on wearer's health. In some other embodiments, the opening 126 may not be needed for example, in cases when the proposed wristband 100 is configured for use with conventional wristwatches.

According to the embodiment, the fifth portion 112 of the main body 102 includes an opening 124 configured thereon, and the fourth portion 110 of the main body 102 includes an opening 125 configured thereon as seen in FIG. 4. The distal end of the band 116 is inserted through the opening 124 and looped around the wearer's wrist such that a first segment 116a of the band 116 extends over a length of a second segment 116b of the band 116 ensuring one of the loop holes from the set of loop holes 120 present in the first segment of the first band 116 is received and retained by the retainer member 117 selectively configured on one of the loop holes from the set of loop holes 120 present in the second segment of the band 116 as seen in FIG. 13. Similarly, the far end of the band 118 is looped around the wearer's thumb such that one of the loop holes from the set of loop holes 122 of the band 118 is received, and retained by a retainer member 119 configured over the opening 125 of the fourth portion 110 of the main body 102

Figure 8:
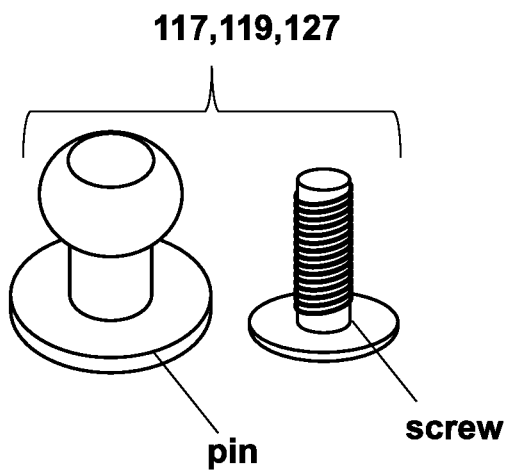
FIG. 8 illustrates an exemplary pin screw set used to receive and retain the first and second bands when looped around the wrist and thumb of the wearer respectively, according to an embodiment of the present invention.

According to the embodiment, the retainer member 117, the retainer member 119 and the retainer member 127 preferably includes but not limited to a pin and screw set (as seen in FIG. 8) mounted on selected hole from the set of loop holes 120 positioned on the band 116, the opening 125 located on the fourth portion 110 of the main body 102, and the selected hole from the set of holes 123 positioned in proximity to the sixth portion 114 of the main body 102, respectively.

Figure 7:
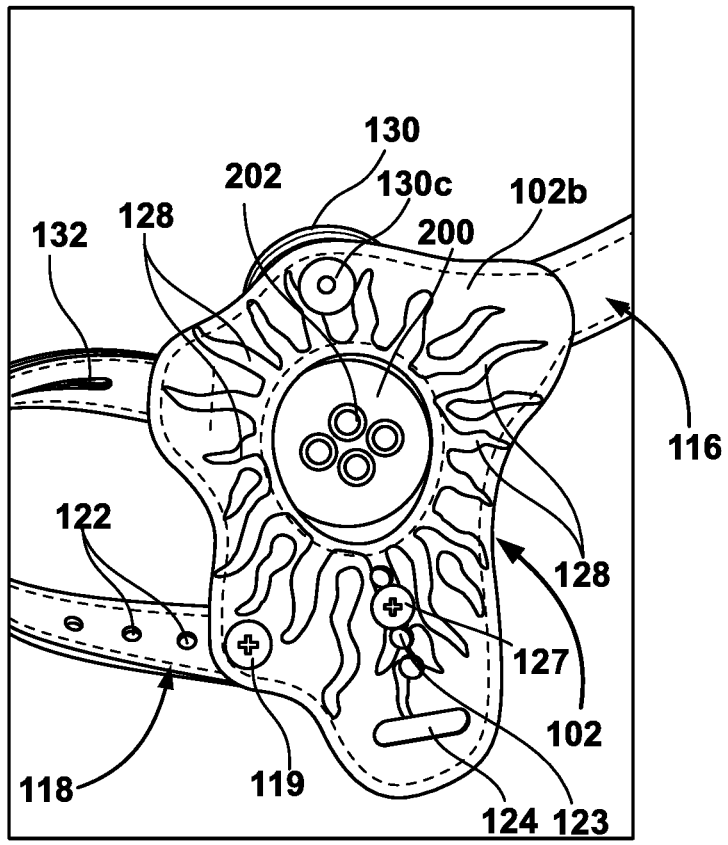
FIG. 7 illustrates a sectional view of the wristband particularly the bottom surface of a main body of the wristband, according to an embodiment of the present invention.

According to the embodiment of the present invention, the bottom surface 102b of the main body 102 may further include a plurality of breathable grooves 128 configured around the opening or center opening 126 of the main body 102. The grooves 128 are configured for moisture removal from the wrist portion covered by the wristband 100. This grooves 128 allows atmospheric air to get inside the wristband 100 and lets the moisture accumulated around the covered wrist region to escape out. The grooves 128 as shown configured in FIGS. 5 and 7 are formed to resemble sun rays. However, it should be understood that the grooves 128 may be formed in many different patterns or shapes. In an example, the breathable grooves 128 may preferably be formed using but not limited to a hot pressing process.

The wristband or watchband 100 with the wrist wearable device 200 (such as the smartwatch), when worn by a wearer 300 by looping and securing the band 116 around the wearer's wrist, and the band 118 around the wearer's thumb, the main body 102 holding the wrist wearable device or smartwatch 200 would position a face portion of the wrist wearable device 200 in a natural line of sight or a very convenient line of sight for the wearer 300, while the wearer 300 is performing different activities such as writing, holding a steering wheel of a vehicle, riding a bike, during running and so on, as collectively seen in FIGS. 2 and 13. In an example shown in FIG. 14, the proposed wristband 100 is shown in use worn by a biker 300 (the wearer of the wristband 100) with the positioning of the face of the smartwatch 200 in a natural line of sight or convenient line of sight for the rider 300, while the rider 300 is riding a bike/bicycle 400. The proposed ergonomically designed wristband 100 eliminates necessity of turning a wearer's arm to view the face portion of the smartwatch 200 and thus the wearer 300 can comfortably keep performing the activities (such as riding the bike in this example) without compromising the safety.

Further, unlike many of the traditional watchbands, when the wearer is wearing gloves, or long sleeve shirts, the face of the watch is often concealed under the sleeve portion of the gloves or shirts, the proposed wristband 100 is structurally configured in a way so that it can be comfortably worn over the sleeves of the gloves 500 as seen in FIG. 12. The length of the bands 116 and 118 are chosen such that the wristband 100 is not just limited to its use on bare hands but also over the gloves or even over the sleeves of the shirt.

Further in the context of the present invention, the lengths for the bands 116 and 118 may be chosen such that the proposed wristband 100 can be constructed and be widely used by small children or adults with wrist sizes ranging from 13 cm to 24 cm. Further, it should be understood that the proposed wristband 100 can be configured for both left hander and the right hander users. As will be appreciated by those skilled in the art, one just need to mirror the main body portion 102 of the wristband 100 in order to construct the wristbands for the right hand and the left hand.

The wristband 100 and associated components thereof may be made using variety of materials and in different shapes and sizes, and thus one should consider the use of substitute elements to be within the realm of the present disclosure and claims.

Although particular embodiments of the invention have been described in detail for purposes of illustration, various modifications and enhancements may be made without departing from the spirit and scope of the invention.

What is claimed is:

1. An ergonomic wristband (100) for a wrist wearable device (200), comprising:
   a main body (102) comprising a top surface (102a), a bottom surface (102b), a first portion (104), a second portion (106), a third portion (108), a fourth portion (110), a fifth portion (112), and a sixth portion (114);
   a first band (116) comprising a proximal end and a distal end, the first band (116) is attached to the first portion (104) of the main body (102) at the proximal end, and includes a first set of loop holes (120) extending between the proximal end and the distal end;
   a second band (118) comprising a near end and a far end, the second band (118) is attached to the second portion (106) of the main body (102) and includes a second set of loop holes (122) extending between the near end and the far end;
   at least one coupling (130) used for releasably attaching the wrist wearable device (200) in between the third portion (108) and a point in proximity to the fifth portion (112) of the main body (102) such that when attached, a back portion of the wrist wearable device (200) is laid over the sixth portion (114) of the main body (102);
   wherein the fifth portion (112) of the main body (102) includes a first opening (124) through which the distal end of the first band (116) is inserted and looped around a wearer's wrist such that a first segment (116a) of the first band (116) extends over a length of a second segment (116b) of the first band (116) ensuring one of the loop holes from the first set of loop holes (120) present in the first segment of the first band (116) is received and retained by a first retainer member (117) configured on one of the loop holes from the first set of loop holes (120) present in the second segment of the first band (116);
   wherein the fourth portion (110) of the main body (102) comprising a second retainer member (119) configured thereon, wherein the far end of the second band (118) is looped around a wearer's thumb such that one of the loop holes from the second set of loop holes (122) of the second band (118) is received, and retained by the second retainer member (119); and
   wherein, the wristband (100) with the wrist wearable device (200), when worn by a wearer (300) by looping and securing the first band (116) around the wearer's wrist, and the second band (118) around the wearer's thumb, the main body (102) positions a face portion of the wrist wearable device (200) in a natural line of sight or a very convenient line of sight for the wearer (300) thereby preventing necessity of turning a wearer's arm to view the face portion of the wrist wearable device (200).

2. The wristband (100) of claim 1, wherein the wrist wearable device (200) comprising at least one of: a wristwatch, a smartwatch, and an electronic device with a display.

3. The wristband (100) of claim 1, wherein the second band (118) further comprising an incision (132) of a predefined length made thereon in proximity to the second portion (106) of the main body (102).

4. The wristband (100) of claim 3, wherein the incision (132) present on the second band (118) retains flexibility of the second band (118) providing comfort in thumb's movement when the second band (118) is looped and secured around the wearer's thumb.

5. The wristband (100) of claim 1, wherein the first retainer member (117) and the second retainer member (119) comprising a pin and screw set mounted on one of the holes from the first set of loop holes (120) positioned on the first band (116), and a second opening (125) located on the fourth portion (110) of the main body (102) respectively.

6. The wristband (100) of claim 1, wherein the main body (102) includes a third opening (126) configured on the sixth portion (114) of the main body (102) and is made substantially egg-shaped or circular shaped.

7. The wristband (100) of claim 1, wherein the at least one coupling (130) snappingly attaches the wrist wearable device (200) in between the third portion (108) and the point in proximity to the fifth portion (112) of the main body (102).

8. The wristband (100) of claim 1, wherein the at least one coupling (130) snappingly attaches a first side of the wrist wearable device (200) to the third portion (108) of the main body (102).

9. The wristband (100) of claim 1 further comprising a set of holes (123) positioned in between the sixth portion (114) and the fifth portion (112) of the main body (102).

10. The wristband (100) of claim 9, wherein the set of holes (123) are configured to selectively hold a third retainer member (127) in order to facilitate accommodation of different sizes of the wrist wearable devices (200) in between the third portion (108) of the main body (102) and a selected hole from the set of holes (123).

11. The wristband (100) of claim 10, wherein the third retainer member (127) is configured to receive a hole (130a) present in the at least one coupling (130) that attaches one side of the wrist wearable device (200) to the selected hole from the set of holes (123).

12. The wristband (100) of claim 1, wherein the main body (102) comprising at least a first layer (101a), a second layer (101b), and a third layer (101c).

13. The wristband (100) of claim 12, wherein the first layer (101a) and the second layer (101b) are made identical in shape using same or different material and are attached embodying the third layer (101c) therebetween.

14. The wristband (100) of claim 13, wherein the material is selected from a group consisting of a leather, plastic, silicone, rubber, elastic polymer, or other suitable resilient material.

15. The wristband (100) of claim 13, wherein the third layer (101c) is made of a polycarbonate film that helps at least the wristband (100) in achieving an ergonomic curve over the wearer's wrist when worn by the wearer (300), or the main body (102) of the wristband (100) to securely hold the wrist wearable device (200) in position.

16. The wristband (100) of claim 13, wherein the third layer (101c) is glued to attach to the first layer (101a) and the second layer (101b), and includes a plurality of holes (101d) that lets the glue to effectively pass over undersides of the first layer (101a) and the second layer (101b) attaching to the third layer (101c).

17. The wristband (100) of claim 1, wherein the bottom surface (102b) of the main body (102) comprising a plurality of breathable grooves (128) configured around the third opening (126) on the sixth portion (114) of the main body (102) for moisture removal.

* * * * *